US007855174B2

(12) United States Patent
Boyle

(10) Patent No.: US 7,855,174 B2
(45) Date of Patent: Dec. 21, 2010

(54) METHODS OF TREATING VASODILATORY SHOCK

(75) Inventor: Walter A. Boyle, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 12/235,062

(22) Filed: Sep. 22, 2008

(65) Prior Publication Data

US 2009/0143294 A1 Jun. 4, 2009

Related U.S. Application Data

(60) Provisional application No. 60/974,096, filed on Sep. 21, 2007.

(51) Int. Cl.
*A61K 31/00* (2006.01)
*A61K 35/56* (2006.01)
*A61K 35/00* (2006.01)

(52) U.S. Cl. .............................. 514/1; 424/520; 514/2

(58) Field of Classification Search ........................ None
See application file for complete search history.

(56) References Cited

PUBLICATIONS

Landry et al. The pathogenesis of vasodilatory shock. N Eng J Med. 2001; 345(8):588-595.*
Li J et al. Peroxynitrite-induced relaxation in isolated rat aortic rings and mechanisms of action. Toxicol Appl Pharmacol. 2005; 209:269-276.*
Li W et al. Cocaine-induced relaxation of isolated rat aortic rings and mechanisms of action: possible relation to cocaine-induced aortic dissection and hypotension. Eur J Pharmacol. 2004; 496:151-158.*
Xu et al. The role of calcium desensitization in vascular hyporeactivity and its regulation after hemorrhagic shock in the rat. Shock, 2005; 23(6):576-581.*
Bolz S et al. Nitric oxide-induced decrease in calcium sensitivity of resistance arteries is attributable to activation of the myosin light chain phosphatase and antagonized by the RhoA/Rho kinase pathway. Circulation, 2003; 107:3081-3087.*
Liu H-P et al. Myosin phosphatase inhibiton restores catecholamine sensitivity in vasodilatory shock. (Meeting Abstract) Anesthesiology, Oct. 15, 2007; 107:A1320.*
Zhao K-S et al. New approach to treatment of shock—restitution of vasoreactivity. Shock, 2002; 18(2):189-192.*
Abderrahmane, A., et al., "The Large Conductance, Voltage-dependent, and Calcium-sensitive K+ Channel, Hslo, Is a Target of cGMP-dependent Protein Kinase Phosphorylation in Vivo," The Journal of Biological Chemistry, Dec. 4, 1998, pp. 32950-32956, vol. 273, No. 49.
"Part 6: Advanced Cardiovascular Life Support, Section 6: Pharmacology II: Agents to Optimize Cardiac Output and Blood Pressure," Resuscitation, 2002, pp. 155-162, vol. 46.
Benedict, C., et al., "Arterial Norepinephrine Changes in Patients with Septic Shock," Circulatory Shock, 1992, pp. 165-172, vol. 38.

Boyle, W., et al., "iNOS Gene Expression Modulates Microvascular Responsiveness in Endotoxin-challenged Mice," Circulation Research, Sep. 29, 2000, pp. 1-7.
Chernow, B., et al., "Pharmacologic Manipulation of the Peripheral Vasculature in Shock: Clinical and Experimental Approaches," Circulatory Shock, 1986, pp. 141-155, vol. 18.
Cobb, J., "Use of nitric oxide synthase inhibitors to treat septic shock: the light has changed from yellow to red," Critical Care Medicine, 1999, pp. 855-856, vol. 27, No. 5.
Dimopoulos, G., et al., "Ca2+-Dependent Rapid Ca2+ Sensitization of Contraction in Arterial Smooth Muscle," Circulation Research, Jan. 5-19, 2007, pp. 121-129.
Dünser, M., et al., "Arginine Vasopressin in Advanced Vasodilatory Shock, A Prospective, Randomized Controlled Study," Circulation, May 13, 2003, pp. 2313-2319.
Etter, E, et al., "Activation of Myosin Light Chain Phosphatase in Intact Arterial Smooth Muscle During Nitric Oxide-induced Relaxation," The Journal of Biological Chemistry, Sep. 14, 2001, pp. 34681-34685, vol. 276, No. 37.
Evans, N., et al., "Inhibition by calyculin A and okadaic acid of the Ca2+ release-activated Ca2+ entry pathway in rat basophilic leukemia cells: Evidence for regulation by Type 1/2A serine/threonine phosphatase activity," Biochimica et Biophysica Acta, 2005, pp. 32-43, 1718.
Fukao, M., et al., "Cyclic GMP-dependent Protein Kinase Activities Cloned BKCa Channels Expressed in Mammalian Cells by Direct Phosphorylation of Serine 1072," The Journal of Biological Chemistry, Apr. 16, 1999, pp. 10927-10935, vol. 274, No. 16.
Hollenberg, S., et al., "Nitric oxide synthase inhibition reverses arteriolar hyporesponsiveness to catecholamines in septic rats," Am. J. Physiol., 1993, pp. H.660-H663, vol. 264.
Ishihara, H., et al., "Calcium-independent Activation of Contractile Apparatus in Smooth Muscle by Calyculin-A1," The Journal of Pharmacology and Experimental Therapeutics, Apr. 10, 1989, pp. 388-396, vol. 250, No. 1.
Jaggar, J., et al., "Calcium sparks in smooth muscle," Am. J. Physiol Cell Physiol, 2000, pp. 233-256, vol. 278.
Karim, S., et al., "Vascular Reactivity in Heart Failure," Circ. Res., 2004, pp. 612-618, vol. 95.
Kato, Y., et al., "Calyculins, Potent Antitumour Metabolites From the Marine Sponge Discodermia Calyx: Biological Activities," Drugs Exptl. Clin. Res., 1988, pp. 723-728, XIV(12).
Kilbourn, R., "Nitric oxide synthase inhibitors—A mechanism-based treatment of septic shock," Crit. Care Med., 1999, pp. 857-858, vol. 27, No. 5.
Leone, M., et al., "Decreased vasopressin responsiveness in vasodilatory septic shock-like conditions," Crit. Care Med., 2006, pp. 1126-1130, vol. 34, No. 4.
Lincoln, T., et al., "Signal Transduction in Smooth Muscle Invited Review: cGMP-dependent protein kinase signaling mechanisms in smooth muscle: from the regulation of tone to gene expression," J. Appl. Physiol., 2001, pp. 1421-1430, vol. 91.
Murphy, M., et al., "Nitric oxide hyperpolarizes rabbit mesenteric arteries via ATP-sensitive potassium channels," The Journal of Physiology, 1995, pp. 47-58, vol. 486.
Parekh, A., et al., "Depletion of InsP3 stores activates a Ca2+ and K+ current by means of a phosphatase and a diffusible messenger," Nature, Aug. 26, 1993, pp. 814-818, vol. 364.

(Continued)

*Primary Examiner*—Elizabeth C. Kemmerer
*Assistant Examiner*—Kimberly A. Ballard
(74) *Attorney, Agent, or Firm*—Polsinelli Shughart PC

(57) ABSTRACT

The invention encompasses methods of decreasing the lumenal diameter of a blood vessel by contacting the vessel with a myosin light chain phosphatase inhibitor.

3 Claims, 10 Drawing Sheets

PUBLICATIONS

Quayle, J., et al., "ATP-Sensitive and Inwardly Rectifying Potassium Channels in Smooth Muscle," Physiological Reviews, Oct. 1997, pp. 1165-1232, vol. 77, No. 4.

Schmidt, H., et al., "The nitric oxide and cGMP signal transduction system: regulation and mechanism of action," Biochimica et Biophysica Acta, 1993, pp. 153-175, vol. 1178.

Somlyo, A., et al., "Ca2+ Sensitivity of Smooth Muscle and Nonmuscle Myosin II: Modulated by G Proteins, Kinases, and Myosin Phosphatase," Physiol. Rev., 2003, pp. 1325-1358, vol. 83.

Surks, H., et al., "Regulation of Myosin Phosphatase by a Specific Interaction with cGMP-Dependent Protein Kinase 1α," Science, Nov. 19, 1999, pp. 1583-1587, vol. 286.

Webb, R., "Smooth Muscle Contraction and Relaxation," Adv. Physiol. Educ., 2003, pp. 201-206, vol. 27.

Yano, Y., et al., "Cytoskeletal reorganization of human platelets inducted by the protein phosphatase 1/2A inhibitors okadaic acid and calyculin A," Biochem J., 1995, pp. 439-449, vol. 307.

* cited by examiner

METHODS OF TREATING VASODILATORY SHOCK

CROSS REFERENCE TO RELATED APPLICATIONS

This application claims the priority of U.S. provisional application No. 60/974,096, filed Sep. 21, 2007, which is hereby incorporated by reference in its entirety.

FIELD OF THE INVENTION

The invention encompasses methods of decreasing the lumenal diameter of a blood vessel.

BACKGROUND OF THE INVENTION

Vasodilatory septic shock is characterized by low arterial blood pressure due to vasodilation with decreased systemic vascular resistance (Landry D W, 2001). This is due to hyporesponsiveness of resistance arteries to endogenous vasopressor agents and vasopressor depletion (Landry 2001; Boyle 2000; Leone and Boyle, 2006). Following volume resuscitation exogenous administration of vascular smooth muscle receptor agonists are thus required to maintain blood pressure and critical organ perfusion (The American Heart Association 2000). Catecholamines—usually either dopamine or norepinephrine—are considered the first line agonists of choice, although progressive hyposensitivity to these agonists often leads to progressive increases in catecholamine requirements to maintain blood pressure. This can result in a vicious cycle in which adverse cardiac effects of the catecholamines— including supraventricular tachyarrhythmias and myocardial ischemia—contribute to further increases in catecholamine requirements with mortality rates that approach 100% (Chernow 1986, Goldstein 2000).

It is apparent that vasodilatation and hypotension are due to failure of the vascular smooth muscle to respond to catecholamines (Benedict and Rose, 1992) and addition of the potent endogenous vasoconstrictor arginine vasopressin (AVP), to catecholamine infusions, has recently been shown to be effective in stabilizing blood pressure and catecholamine requirements in patients with catecholamine-resistant vasodilatory shock (Landry 2001, Dunser 2003, Boyle ASA 2006 review lecture). However, vasoconstriction produced by vasopressin, and the synergistic vasoconstriction produced by the combinations of norepinephrine and vasopressin, was, like responses to norepinephrine alone, decreased in vasodilatory shock (Boyle and Leone, 2006). Thus, while there is a well-described vasopressin deficiency in vasodilatory septic shock, the decrease in vasopressin responsiveness also contributes to a state of relative vasopressin insufficiency, similar to the state of relative catecholamine deficiency, in this condition.

The hyporesponsiveness of vascular smooth muscle to receptor agonists is largely due to de novo expression of inducible nitric oxide synthase (iNOS) and excessive production of NO in vascular smooth muscle (Boyle 2000). NO synthase (NOS) inhibitors have been shown to effectively reverse this hyporesponsiveness and treat the life threatening hypotension that occurs in vasodilatory shock (Boyle 2000, Kilborne 1999). Unfortunately, NO is a ubiquitous mediator, and the pervasive effects of the iNOS inhibitors in vasodilatory shock resulted in increased mortality when these agents were administered in human clinical trials (Cobb 1999).

In the absence of any effective alternative, the current approach for the treatment of vasodilatory shock continues to be administration of large doses of vasoconstrictor agonists, typically norepinephrine or combinations of norepinephrine and vasopressin, to maintain blood pressure and critical organ perfusion. Progressive hyposensitivity to these agonists, however, remains a significant clinical problem that can lead to refractory shock with a high mortality. There is a need in the art, therefore, for a treatment of vasodilatory shock that addresses the vascular smooth muscle hyposensitivity to vasocontrictors.

SUMMARY OF THE INVENTION

One aspect of the invention encompasses a method for decreasing the lumenal diameter of a blood vessel. The method typically comprises contacting the vessel with a myosin light chain phosphatase inhibitor.

Another aspect of the invention encompasses a method for substantially restoring blood vessel sensitivity to a vasoconstrictor. The method generally comprises contacting the vessel with a myosin light chain phophatase inhibitor and the vasoconstrictor.

Yet another aspect of the invention encompasses a method for treating vasodilatory shock in a subject. The method usually comprises administering a myosin light chain phosphatase inhibitor to the subject.

Other aspects and iterations of the invention are described in more thoroughly below.

REFERENCE TO COLOR FIGURES

The application file contains at least one photograph executed in color. Copies of this patent application publication with color photographs will be provided by the Office upon request and payment of the necessary fee.

DETAILED DESCRIPTION OF THE INVENTION

Figure 1:
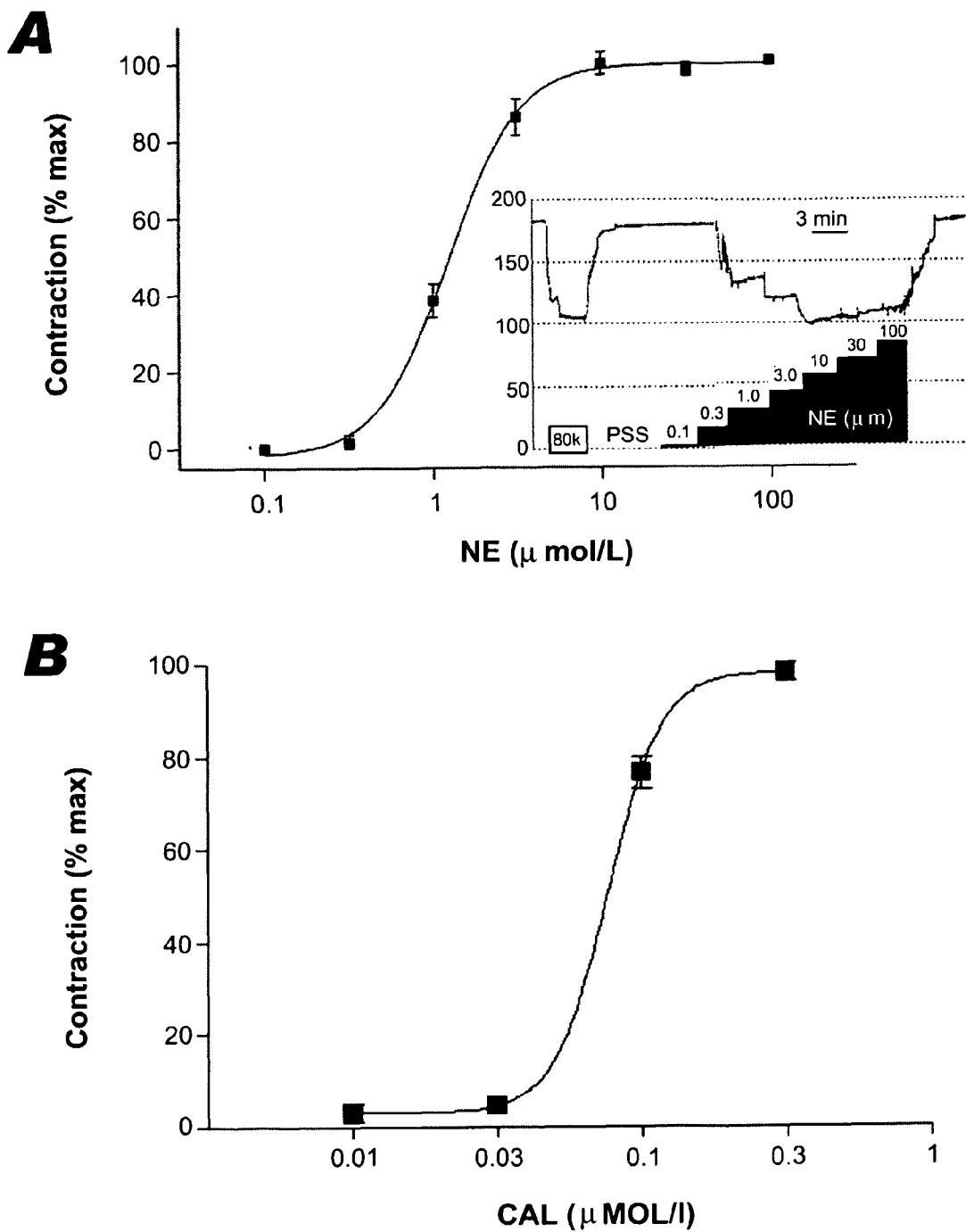
FIG. 1 depicts a series of graphs showing concentration-dependent vessel contraction produced by three different compounds. A. Concentration-dependent contraction produced by NE in rat mesenteric arteries. Inset shows similarity between the maximum contraction produced by NE compared to high $K^+$ (80 mmol/L). B. Concentration-dependent contraction produced by the MLCP inhibitor CAL. C. Concentration-dependent relaxation produced by the NO donor SNP on vessels precontracted with $3\times10^{-6}$ mol/L NE.

The present invention provides methods of utilizing a myosin light chain phosphatase (MLCP) inhibitor to decrease the lumenal diameter of a blood vessel and/or to restore blood vessel sensitivity to a vasoconstricting agent. Accordingly, the invention also provides methods of using a MLCP inhibitor to treat vasodilatory shock.

Generally speaking, without being bound to any particular theory, vascular smooth muscle cell agonists produce vessel contraction via increases in myosin light chain (MLC) phosphorylation. In some instances, MLC is phorphorylated at the serine 19 position. Typically, the MLCP inhibitor of the invention inhibits MLCP from de-phosphorylating MLC. For example, the MLCP inhibitor may inhibit MLCP from de-phosphorylating serine 19 of MLC. A suitable MLCP inhibitor may completely block the de-phosphorylation of MLC, partially block the de-phosphorylation of MLC, or slow the kinetics of the de-phosphorylation of MLC. In some embodiments, a MLCP inhibitor may completely block the de-phosphorylation of serine 19 of MLC, partially block the de-phosphorylation of serine 19 of MLC, or slow the kinetics of the de-phosphorylation of serine 19 of MLC. In other embodiments, a MLCP inhibitor may completely block the de-phosphorylation of other serine or threonine residues of MLC, partially block the de-phosphorylation of other serine or threonine residues of MLC, or slow the kinetics of the de-phosphorylation of other serine or threonine residues of MLC.

MLCP inhibitors may include inhibitors that enzymatically or non-enzymatically block MLCP's activity. Preferably, enzymatic inhibitors are reversible inhibitors. Non-enzymatic inhibitors may include small molecule or pharmacological inhibitors that inhibit the de-phosphorylation of MLC. MLCP inhibitors may affect the activity of MLCP directly or indirectly. In each of the above embodiments, the MLCP inhibitor may inhibit the de-phosphorylation of serine 19 of MLC.

In one embodiment, the MLCP inhibitor may be selected from the group of inhibitors comprising microcystin-LR, tautomycin, okadaic acid, and calyculin A. In another embodiment, the MLCP inhibitor is microcystin-LR. In still another embodiment, the MLCP inhibitor is tautomycin. In yet another embodiment, the MLCP inhibitor is okadaic acid. In still yet another embodiment, the MLCP inhibitor is calyculin A.

In a preferred embodiment, the MLCP inhibitor is specific for MLCP. In this context, specific means that the MLCP inhibitor selectively inhibits MLCP over other phosphatases. Selectivity, as used herein, refers to an MLCP inhibitor that has an $IC_{50}$ for MLCP that is, generally speaking, about $10^1$ to about $10^3$ greater than other phosphatases. In one embodiment, the MLCP inhibitor may have an $IC_{50}$ for MLCP that is about $10^1$, about $5\times10^1$, about $10^2$, about $5\times10^2$, or about $10^3$ greater than other phosphatases. Typically, an MLCP inhibitor has an $IC_{50}$ of about $10^{-9}$ to about $10^{-6}$M for MLCP. In some embodiments, the MLCP inhibitor may have an $IC_{50}$ of about $10^{-10}$, about $5\times10^{-9}$, about $10^{-9}$, about $5\times10^{-8}$, about $10^{-8}$, about $5\times10^{-7}$, $10^{-7}$, $5\times10^{-6}$, $10^{-6}$, $5\times10^{-5}$, $10^{-5}$, $5\times10^{-4}$, or $10^{-4}$ for MLCP.

i. Method of Decreasing the Lumenal Diameter of a Blood Vessel

One aspect of the present invention encompasses a method for decreasing the lumenal diameter of a blood vessel. Typically, the method comprises contacting the blood vessel with a MLCP inhibitor. With out being limited by any one theory, it is anticipated that the MLCP inhibitor inhibits the de-phosphorylation of MLC, which in turn promotes vascular smooth muscle contraction, decreasing the lumen of the blood vessel. Methods of contacting a blood vessel with a MLCP inhibitor are well known in the art. For a detailed example of contacting a vessel ex vivo with a MLCP inhibitor, see the Examples below. For contacting a vessel in vivo, see the examples and section iv of the detailed description below.

Generally speaking, the method entails contacting the blood vessel with an amount of MLCP inhibitor that induces vascular smooth muscle contraction, thereby decreasing the lumenal diameter of the blood vessel, but that does not result in cellular death if the method is performed ex vivo, or the death of the subject if the method is performed in vivo. For instance, typically, the amount of MLCP inhibitor may be about 0 μg/kg body weight to about 300 μg/kg body weight, or more. In other words, the amount of the MLCP inhibitor may be about 1 μg/kg, 5 μg/kg, 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, 80 μg/kg, 85 μg/kg, 90 μg/kg, 95 μg/kg, 100 μg/kg, 105 μg/kg, 110 μg/kg, 115 μg/kg, 120 μg/kg, 125 μg/kg, 130 μg/kg, 135 μg/kg, 140 μg/kg, 145 μg/kg, 150 μg/kg, 155 μg/kg, 160 μg/kg, 165 μg/kg, 170 μg/kg, 175 μg/kg, 180 μg/kg, 185 μg/kg, 190 μg/kg, 195 μg/kg, or about 200 μg/kg. In some embodiments, the amount may be more than 200 μg/kg.

In some embodiments, the blood vessel may be further contacted with a second vasoconstrictor. The second vasoconstrictor may be selected such that it affects vasoconstriction via a different molecular pathway than the MLCP inhibitor. Beneficially, depending on the embodiment, this may lower the amount of MLCP inhibitor needed to decrease the lumenal diameter of the blood vessel compared to administering a MLCP inhibitor alone. Alternatively, depending on the embodiment, contacting the vessel with a second vasoconstrictor in conjunction with an MLCP inhibitor may lower the amount of the second vasoconstrictor needed to decrease the lumenal diameter of the blood vessel, compared to administering the second vasoconstrictor alone.

The second vasoconstrictor may be administered simultaneously or sequentially with the MLCP inhibitor. The vasoconstrictor may be an endogenous vasoconstrictor or exogenous vasoconstrictor. As used herein, endogenous refers to a vasoconstrictor that is produced by the subject and is naturally accessible to the vessel in an amount effective to cause vasoconstriction. Exogenous refers to a vasoconstrictor that is not naturally accessible to a vessel in an amount effective to cause vasoconstriction. Exogenous vasoconstrictors, therefore, may encompass a vasoconstrictor that is produced in vivo, but that is applied at higher concentrations, or in a different location than where the vasoconstrictor is normally found in vivo. Exogenous vasoconstrictors may also encompass synthetically produced vasoconstrictors.

Non-limiting examples of vasoconstrictors include chatecolamines, vasopressins, and other endogenous or exogenous vasoconstrictors. Examples of catecholamines may include epinephrine, norepinephrine, and dopamine. Non-limiting examples of vasopressins include argipressin, lypressin (LVP), phenypressin, and vasotocin. In one embodiment, the blood vessel is contacted with both an MLCP inhibitor and a catecholamine. In another embodiment, the blood vessel may be contacted with both an MLCP inhibitor and a vasopressin. In each of the above embodiments, the MLCP inhibitor may be calyculin A.

Typically, the amount of second vasoconstrictor administered to decrease the lumenal diameter of the blood vessel can and will vary with the condition of the blood vessel. Additionally, one of ordinary skill in the art will appreciate that the amount of second vasoconstrictor administered depends, in part, on the second vasoconstrictor used. For instance, if the second vasoconstrictor is norepinephrine or epinephrine, the amount administered may be between about 0.1 µg/min to about 200 µg/min. In some embodiments, the amount may be about 10 µg/min, 20 µg/min, 30 µg/min, 40 µg/min, 50 µg/min, 60 µg/min, 70 µg/min, 80 µg/min, 90 µg/min, 100 µg/min, 110 µg/min, 120 µg/min, 130 µg/min, 140 µg/min, 150 µg/min, 160 µg/min, 170 µg/min, 180 µg/min, 190 µg/min, or about 200 µg/min. In some embodiments, the amount is more than 200 µg/min.

If the second vasoconstrictor is dopamine, the amount administered may be between about 2 ug/kg/min to about 30 ug/kg/min. In certain embodiments, the amount may be about 2 µg/kg/min, about 5 µg/kg/min, about 10 µg/kg/min, about 15 µg/kg/min, about 20 µg/kg/min, or about 30 µg/kg/min.

Alternatively, If the second vasoconstrictor is vasopressin, the amount administered may be between about 0.005 U/min to about 1 U/min. In various embodiments, the amount administered may be about 0.005 U/min, 0.01 U/min, 0.05 U/min, 0.1 U/min, 0.5 U/min, or about 1 U/min.

In certain embodiments, the blood vessel may be contacted with an MLCP inhibitor, a second vasoconstrictor, and a third vasoconstrictor. The third vasoconstrictor may be administered simultaneously or sequentially with the MLCP inhibitor or the second vasoconstrictor. The third vasoconstrictor may be selected from the vasoconstrictors listed above. In one embodiment, the blood vessel may be contacted with a MLCP inhibitor, a catecholamine, and a third vasoconstrictor. In another embodiment, the blood vessel may be contacted with a MLCP inhibitor, a vasopressin, and a third vasoconstrictor. In yet another embodiment, the blood vessel may be contacted with a MLPC inhibitor, a catecholamine, and a vasopressin. In each of the above embodiments, the MLCP inhibitor may be calyculin A.

The lumenal diameter of a blood vessel may be decreased ex vivo or in vivo. Methods of measuring blood vessel diameter are well known in the art. For instance, see the materials and methods for Examples 1-2.

ii. Method of Restoring Blood Vessel Sensitivity to a Vasoconstrictor

As detailed above, during vasodilatory shock vessels may show a progressive hyposensitivity to vasodilators that may result in the death of the subject. The invention encompasses, advantageously, a method of substantially restoring blood vessel sensitivity to a vasoconstrictor. This method may be used to treat vasodilatory shock, as detailed below, and may help prevent the progression of vasodilatory shock to refractory shock. As used herein, the phrase "substantially restoring" blood vessel sensitivity to a vasoconstrictor refers to slowing or minimizing the progressive hyposensitivity to vasoconstrictors that is commonly observed in vasodilatory shock. Typically, the method comprises contacting the vessel with a MLCP inhibitor and the vasoconstrictor. As explained above, methods of contacting a blood vessel with a MLCP inhibitor and/or vasoconstrictor are well known in the art. For a detailed example of contacting a vessel ex vivo with a MLCP inhibitor and/or vasoconstrictor, see Example 1 and 2. For contacting a vessel in vivo, see the examples or section iv of the detailed description below.

The method entails contacting the blood vessel with a low amount of MLCP inhibitor that is sufficient to substantially restore blood vessel sensitivity to a vasoconstrictor, but that does not cause contraction of the vascular smooth muscle cells (a "sub-constricting" amount). One skilled in the art will appreciate that the sub-constricting amount can and will vary depending upon the conditions of the blood vessel. The sub-constricting amount may be determined, however, using the methods detailed in the Examples.

In certain embodiments, the MLCP inhibitor may be administered at a sub-constricting amount producing plasma concentrations between about $1 \times 10^{-9}$M and about $1 \times 10^{-4}$M. In one embodiment, the MLCP inhibitor may be administered to produce plasma concentrations between about $10^{-9}$M and about $10^{-8}$M. In another embodiment, the MLCP inhibitor may be administered at an amount between about $10^{-8}$M and about $10^{-7}$M. In an alternative embodiment, the MLCP inhibitor may be administered to produce plasma concentrations about equal too or less than $3 \times 10^{-8}$M.

Stated another way, the amount of MLCP inhibitor administered may be about 0 µg/kg body weight to about 300 µg/kg body weight, or more. In other words, the amount of the MLCP inhibitor may be about 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 105 µg/kg, 110 µg/kg, 115 µg/kg, 120 µg/kg, 125 µg/kg, 130 µg/kg, 135 µg/kg, 140 µg/kg, 145 µg/kg, 150 µg/kg, 155 µg/kg, 160 µg/kg, 165 µg/kg, 170 µg/kg, 175 µg/kg, 180 µg/kg, 185 µg/kg, 190 µg/kg, 195 µg/kg, or about 200 µg/kg. In some embodiments, the amount may be more than 200 µg/kg.

Substantially restoring blood vessel sensitivity to a vasoconstrictor may be performed ex vivo or in vivo. Methods of measuring blood vessel sensitivity to a vasoconstrictor are known in the art. For instance, see Example 1.

The vasoconstrictor may be an endogenous vasoconstrictor or exogenous vasoconstrictor, as defined above. Non-limiting examples of vasoconstrictors include chatecolamines, vasopressins, and other endogenous or exogenous vasoconstrictors. Non-limiting examples of catecholamines include epinephrine, norepinephrine, and dopamine. Non-limiting examples of vasopressins include argipressin, lypressin (LVP), phenypressin, and vasotocin. In one embodiment, the sensitivity of a blood vessel to a catecholamine is substantially restored. In another embodiment, the sensitivity of a blood vessel to norepinephrine is substantially restored. In yet another embodiment, the sensitivity of a blood vessel to a vasopressin is substantially restored. In still yet another embodiment, the blood vessel sensitivity to an endogenous vasoconstrictor is substantially restored. In still another embodiment, the blood vessel sensitivity to an exogenous vasoconstrictor is substantially restored. In each of the above embodiments, the sensitivity of the blood vessel may be substantially restored by contacting the blood vessel with the MLCP inhibitor calyculin A.

iii. Method of Treating Vasodilatory Shock in a Subject

Another aspect of the invention encompasses a method of treating vasodilatory shock in a subject. Typically, the method comprises administering a MLCP inhibitor to the subject. Without being limited to a particular theory, it is believed that the MLCP inhibitor will both directly decrease the lumenal diameter of the affected blood vessel, and substantially restore the sensitivity of the blood vessel to a vasoconstrictor, thereby inducing vasoconstriction and treating the vasodilatory shock.

Generally speaking, the method entails administrating to the subject an amount of MLCP inhibitor that treats vasodilatory shock, but that does not result in cellular death if the method is performed ex vivo, or the death of the subject if the method is performed in vivo. For instance, typically, the amount of MLCP inhibitor may be about 0 µg/kg body weight to about 300 µg/kg body weight, or more. In other words, the amount of the MLCP inhibitor may be about 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 105 µg/kg, 110 µg/kg, 115 µg/kg, 120 µg/kg, 125 µg/kg, 130 µg/kg, 135 µg/kg, 140 µg/kg, 145 µg/kg, 150 µg/kg, 155 µg/kg, 160 µg/kg, 165 µg/kg, 170 µg/kg, 175 µg/kg, 180 µg/kg, 185 µg/kg, 190 µg/kg, 195 µg/kg, or about 200 µg/kg. In some embodiments, the amount may be more than 200 µg/kg.

The MLCP inhibitor may be administered in a sub-contracting amount. Alternatively, the MLCP inhibitor may be administered in an amount sufficient to induce vascular smooth muscle cell contraction. One skilled in the art will appreciate that the amount administered can and will vary depending upon the severity of the subject's condition.

In a further aspect of the method, a second vasoconstrictor may be administered to the subject. The second vasoconstrictor may be selected such that it affects vasoconstriction via a different molecular pathway than the MLCP inhibitor. Beneficially, depending on the embodiment, this may lower the amount of MLCP inhibitor needed to decrease the lumenal diameter of the blood vessel compared to administering a MLCP inhibitor alone. Alternatively, depending on the embodiment, administering a second vasoconstrictor in conjunction with an MLCP inhibitor may lower the amount of the second vasoconstrictor needed to decrease the lumenal diameter of the blood vessel, compared to administering the second vasoconstrictor alone. The second vasoconstrictor may be administered simultaneously or sequentially with the MLCP inhibitor. In one embodiment, the MLCP inhibitor may be administered first, followed by the second vasoconstrictor. In another embodiment, the second vasoconstrictor may be administered first, followed by the MLCP inhibitor. In yet another embodiment, the MLCP inhibitor and the second vasoconstrictor may be administered simultaneously. The vasoconstrictor may be an endogenous vasoconstrictor or exogenous vasoconstrictor, as defined above. Non-limiting examples of vasoconstrictors include chatecolamines, vasopressins, and other endogenous or exogenous vasoconstrictors. Non-limiting examples of catecholamines include epinephrine, norepinephrine, and dopamine. Non-limiting examples of vasopressins include argipressin, lypressin (LVP), phenypressin, and vasotocin.

In one embodiment, the subject is administered both an MLCP inhibitor and a catecholamine. In another embodiment, the subject is administered both an MLCP inhibitor and norepinephrine. In yet another embodiment, the subject is administered both a MLCP inhibitor and a vasopressin. In an alternative embodiment, the MLCP inhibitor would be administered alone and would restore responsiveness to an endogenous second vasoconstrictor. In each of the above embodiments, the MLCP inhibitor may be calyculin A.

In certain embodiments, the subject may be administered an MLCP inhibitor, a second vasoconstrictor, and a third vasoconstrictor. The third vasoconstrictor may be administered simultaneously or sequentially with the MLCP inhibitor or the second vasoconstrictor. The third vasoconstrictor may be selected from the vasoconstrictors listed above. In one embodiment, the subject may be administered a MLCP inhibitor, a catecholamine, and a third vasoconstrictor. In another embodiment, the subject may be administered a MLCP inhibitor, a vasopressin, and a third vasoconstrictor. In yet another embodiment, the subject may be contacted with a MLPC inhibitor, a catecholamine, and a vasopressin. In each of the above embodiments, the MLCP inhibitor may be calyculin A.

Typically, the amount of second or third vasoconstrictor administered to treat vasodilatory shock can and will vary with the condition of the subject. Additionally, one of ordinary skill in the art will appreciate that the amount of second vasoconstrictor administered depends, in part, on the second vasoconstrictor used. For instance, if the second vasoconstrictor is norepinephrine or epinephrine, the amount administered may be between about 0.1 µg/min to about 200 µg/min. In some embodiments, the amount may be about 10 µg/min, 20 µg/min, 30 µg/min, 40 µg/min, 50 µg/min, 60 µg/min, 70 µg/min, 80 µg/min, 90 µg/min, 100 µg/min, 110 µg/min, 120 µg/min, 130 µg/min, 140 µg/min, 150 µg/min, 160 µg/min, 170 µg/min, 180 µg/min, 190 µg/min, or about 200 µg/min. In some embodiments, the amount may be more than 200 µg/min.

If the second vasoconstrictor is dopamine, the amount administered may be between about 2 ug/kg/min to about 30 ug/kg/min. In certain embodiments, the amount may be about 2 µg/kg/min, about 5 µg/kg/min, about 10 µg/kg/min, about 15 µg/kg/min, about 20 µg/kg/min, or about 30 µg/kg/min.

Alternatively, If the second vasoconstrictor is vasopressin, the amount administered may be between about 0.005 U/min to about 1 U/min. In various embodiments, the amount administered may be about 0.005 U/min, 0.01 U/min, 0.05 U/min, 0.1 U/min, 0.5 U/min, or about 1 U/min.

In each of the above embodiments, the MLCP inhibitor may be administered before the onset of vasodilatory shock, or during vasodilatory shock. In one embodiment, the MLCP inhibitor may be administered during refractory vasodilatory shock.

iv. Forms of Inhibitors and Routes of Administration

The MLCP inhibitors described above may exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof. Pharmaceutically acceptable salts of such tautomeric, geometric or stereoisomeric forms are also included within the invention. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures of R and S forms for each stereocenter present.

In a further embodiment, the inhibitors of the present invention may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with any of the compounds of the invention.

The inhibitors of the present invention may be formulated into pharmaceutical compositions and administered by a number of different means that will deliver a therapeutically effective dose. Such compositions may be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. In one embodiment, the inhibitor may be administered in a bolus. In a preferred embodiment, the inhibitor may be administered intravenously. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Solid dosage forms for oral administration may include capsules, tablets, pills, powders, and granules. In such solid dosage forms, the compound is ordinarily combined with one or more adjuvants appropriate to the indicated route of administration. If administered per os, the compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. For instance, the MLCP inhibitor of the invention may be administered with a carrier. Non-limiting examples of such a carrier include protein carriers and lipid carriers. An example of a protein carrier is albumin. In one embodiment, the MLCP inhibitor may be administered with albumin as a protein carrier. Typically, the carrier would help direct the MLCP inhibitor to the blood vessels of the subject and retain the MLCP inhibitor in the blood vessels of the subject.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The amount of the compound of the invention that may be combined with the carrier materials to produce a single dosage of the composition will vary depending upon the subject and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

DEFINITIONS

As used herein, "subject" refers to a mammal capable of suffering from vasodilatory shock. Subjects may include laboratory animals, such as mice, rats, guinea pigs, or monkeys. Alternatively, subjects may include humans.

As used herein, "treating" is used in its broadest sense to mean effecting vasodilatory shock progression. In an exemplary embodiment, treating means slowing vasodilatory progression in a subject, compared to an untreated subject.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Materials and Methods for Examples 1-2

Animals and Preparation. All studies were approved by the Washington University Animal Studies Committee. The vessel isolation and cannulation methods were similar to those previously described (Tsuneyoshi, Boyle W A 2003). In brief, third order branches of mesenteric arteries (outside diameter, 150-250 µm) were cannulated in a water-jacketed vessel bath in HEPES-buffered physiologic saline solution (PSS) (mM): NaCl 135, NaHCO$_3$ 2.6, Na$_2$HPO$_4$ 0.34, KH$_2$PO$_4$ 0.44, KCl 5, CaCl$_2$ 1.6, MgSO$_4$ 1.17, EDTA 0.025, HEPES 10, and glucose 5.5 (pH=7.35 at 35° C.). The endothelium was denuded by the air bubble method (Tsuneyoshi).

The vessel bath was transferred to the stage of a Nikon Diaphot inverted microscope, and transmural pressure was held constant (40 mm Hg) with a pressure servo system. A computer-based image analysis system (Boyle W A 2003), was used to continually measure and record vessel outside diameter (OD) during contraction and relaxation.

After a 30 min equilibration period, the integrity of the vascular smooth muscle was assessed by treatments with high K$^+$ (80 mM) and norepinephrine (NE, 10$^{-6}$M). Vessels were considered "healthy" if these treatments resulted in robust and uniform constriction along the entire length of the vessel. Vessels that did not respond in this manner were discarded. Endothelial denudation was verified by adding the endothelium-dependent vasodilator, acetylcholine (ACh, 10$^{-5}$M), to the NE-contracted vessel. Vessels which displayed >5% relaxation with ACh were also discarded.

Data Analysis. Responses to agonists are expressed as percent (%) of the maximal contraction during the initial application of high K$^+$ (80 mM) in each vessel according to the following formula: $(OD_{basal} - OD_{measured})/(OD_{basal} - OD_{High\ K^+}) \times 100$.

Contraction values (%) are expressed as the mean±SEM. For dose-response data, the half-maximal effective concentration (EC$_{50}$) was determined from best fit of the dose-response data to the Hill equation using Prism 3.0, Graph Pad Software (San Diego, Calif.). Statistical analysis was performed using two-way analysis of variance followed by Bonferroni with correction for post hoc comparisons. P<0.05 was considered significant.

All Chemicals and pharmacological agents were obtained from reputable and reliable sources. Calyculin A was purchased from Biomol (Plymouth Meeting, Pa.).

Example 1

Figure 1C:
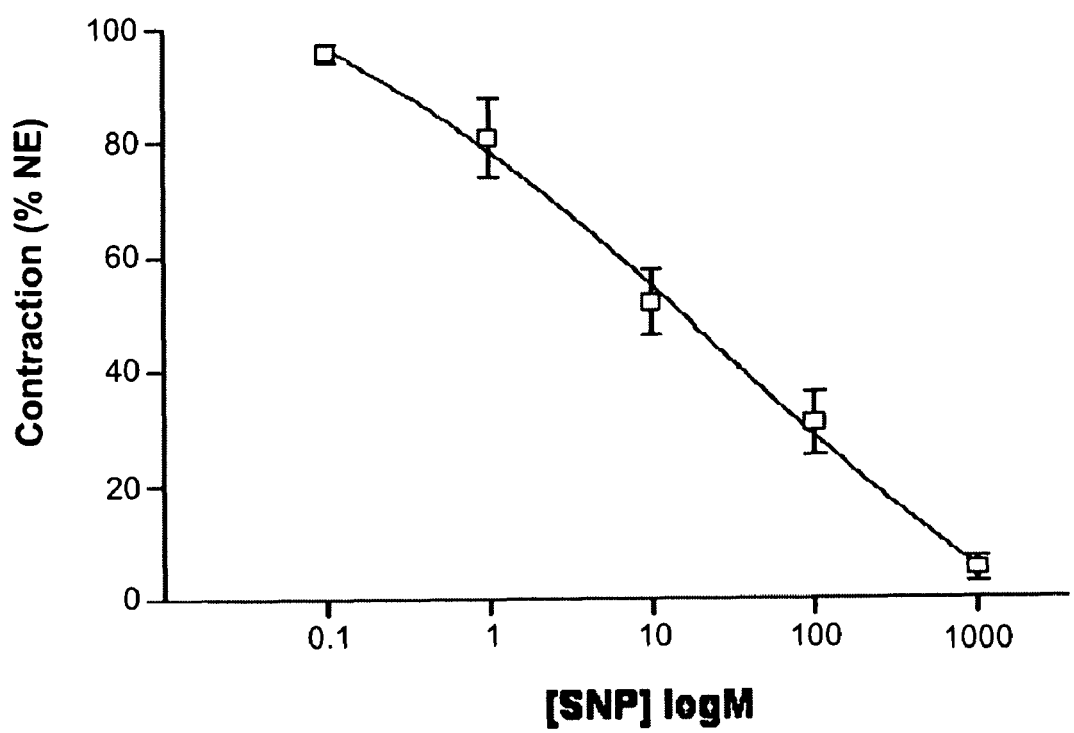

Dose-Response Relationships Between Vessel Contraction and Norepinephrine, Sodium Nitroprusside, and Calyculin A The concentration-contraction relationships for the endogenous vasoconstricting agonist norepinephrine (NE), the nitric oxide (NO) donor, sodium nitroprusside (SNP), and the MLCP inhibitor calyculin A (CAL) are shown in FIG. 1. The concentration-contraction relationship for NE in isolated rat mesenteric arteries is shown in FIG. 1A. NE produced a maximum contraction similar to that produced by high K$^+$ (80 mmol/L) as shown in the inset. As shown in FIG. 1A, the concentration-contraction relationship for NE was well fit by the Hill equation with an EC$_{50}$ of 1.1 µmol/L (n=6). As shown in FIG. 1B, CAL alone produced concentration-dependent smooth muscle contraction with an EC$_{50}$ of 7.7×10$^{-8}$ mol/L. The subcontracting dose of 3×10$^{-8}$ mol/L (n=5) shown was used for subsequent studies. As shown in FIG. 1C, SNP produced concentration-dependent relaxation of vessels pre-contracted with NE (3×10$^{-6}$ mol/L). The concentration-relaxation data for SNP of the NE-pre-contracted vessels were well fit by a Hill equation with an EC$_{50}$ of 2.7×10$^{-5}$ mol/L. The 10$^{-5}$ mol/L SNP concentration as shown resulted in 51.8±5.8% relaxation (n=6) and was used for subsequent studies.

Figure 2:
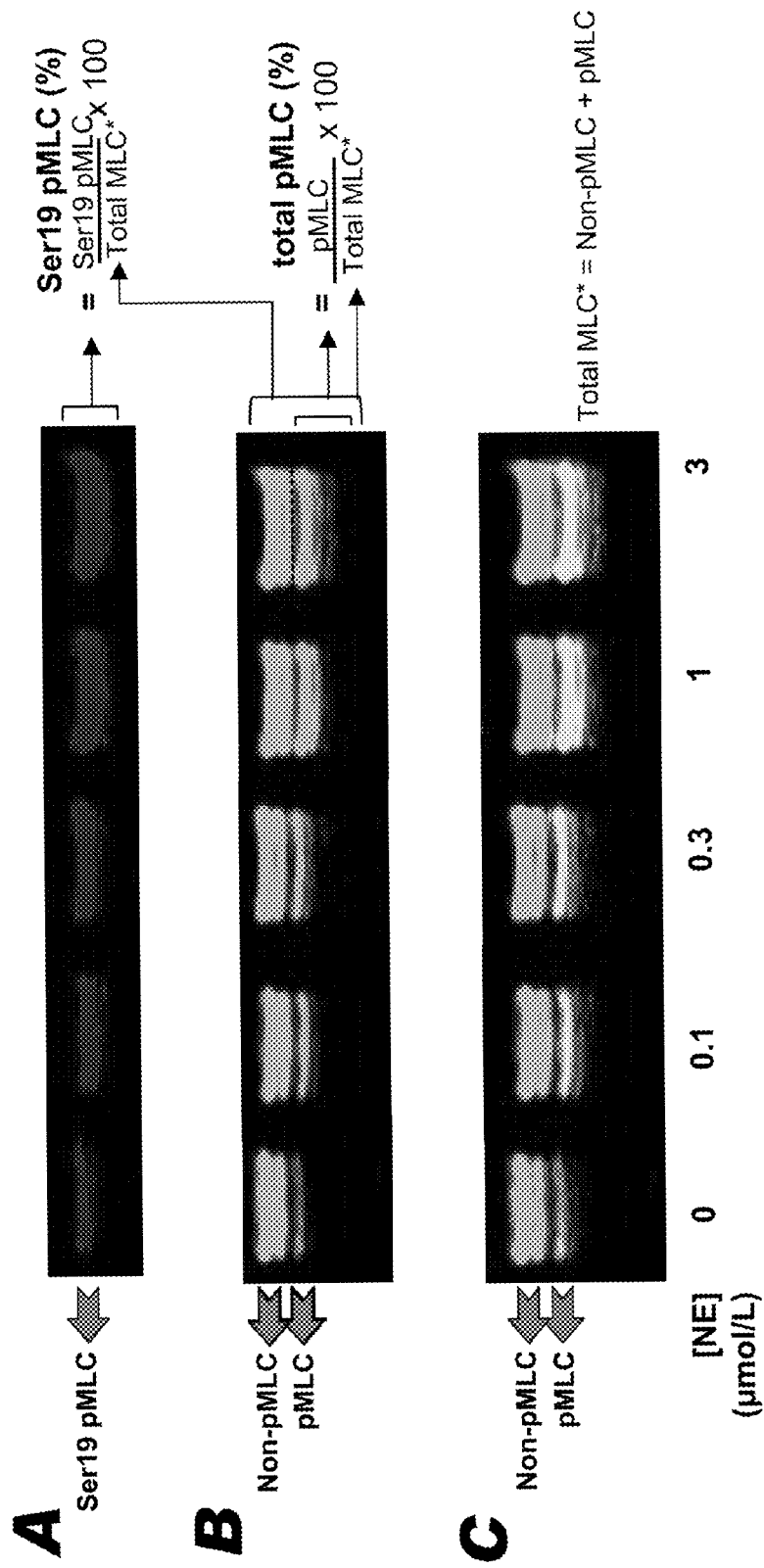
FIG. 2 depicts an image of an immunoblot. Non-phosphorylated and phosphorylated MLC isoforms were separated using UG PAGE. The immunoblots were probed with anti-MLC and anti-phospho-MLC antibody specific for Ser19 monophosphorylated MLC (Ser19 pMLC). Fluorescent signals from the secondary antibodies were analyzed using the Odyssey Infrared Imaging system. Measurement of total MLC phosphorylation (% total pMLC) using the traditional approach of dividing the signal from the phosphorylated bands on a UG immunoblot by the total MLC band signal is shown. Similarly, changes in Ser19 phosphorylation (% Ser19 pMLC) are measured by dividing the Ser19 pMLC antibody signal by the total MLC signal as shown. A represents Ser19 pMLC, B represents pMLC, and C represents an overlay of A and B.
Figure 3:
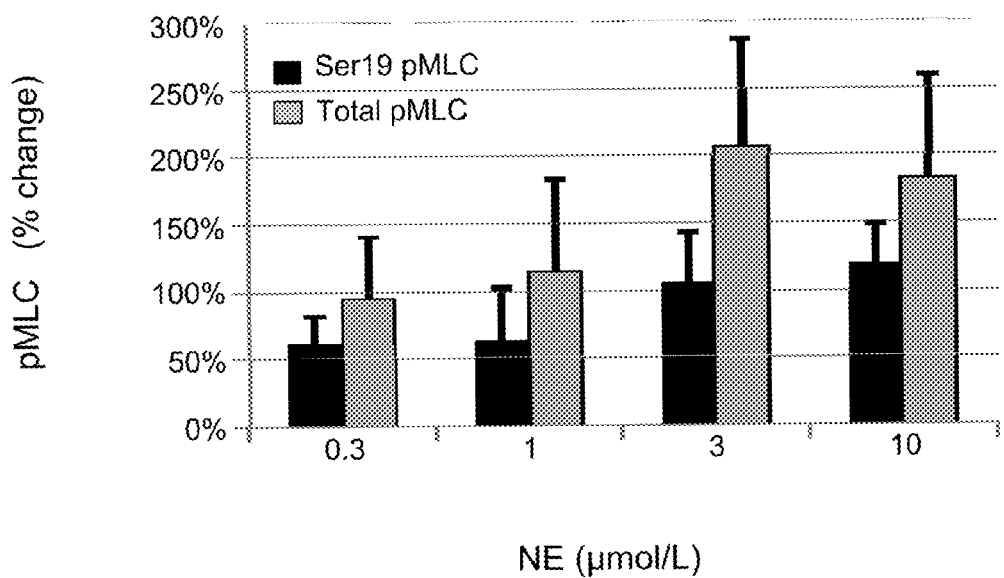
FIG. 3 depicts a series of graphs. Concentration-dependent total pMLC and Ser19 pMLC are shown as % change. A. Both total pMLC and Ser19 pMLC appear to increase proportionally in response to increasing [NE]. B. Increases in [CAL] results in an apparent greater increase in total pMLC suggesting the presence of other MLC phosphorylated species. C. In precontracted vessels with $3\times10^{-6}$ mol/L NE, increasing [SNP] produced a marked decrease in the % change of both total pMLC and Ser19 pMLC.
Figure 3:
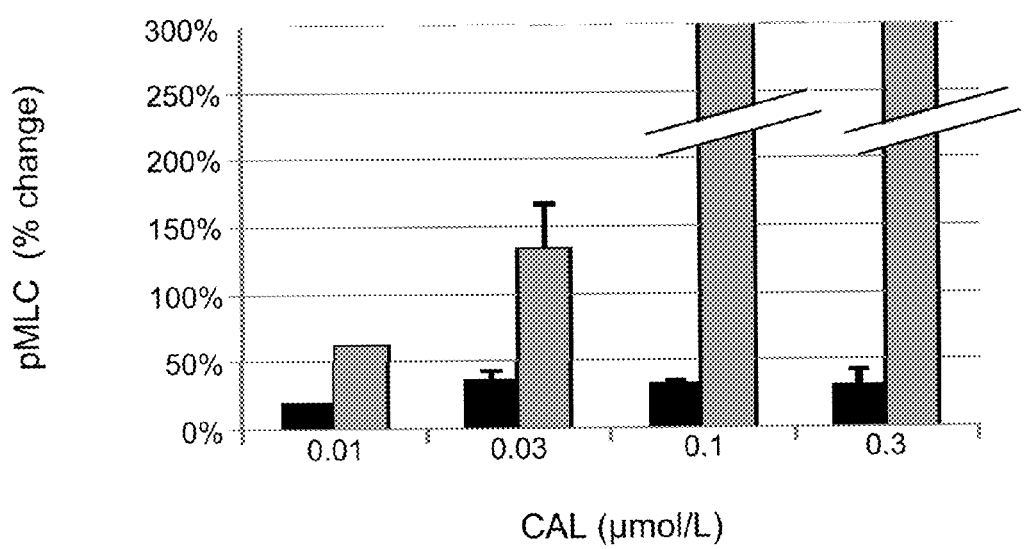
Figure 3C:
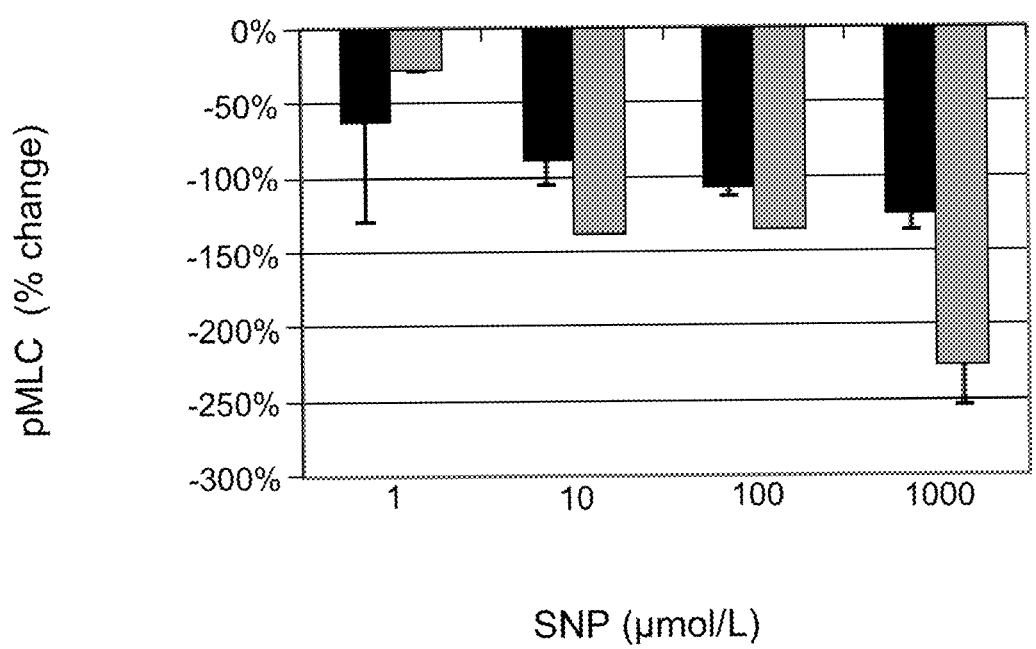

Immunoblots of mesenteric resistance artery homogenates following treatment with NE are shown in FIG. 2, including the method used for determination of % total pMLC and % Ser19 pMLC. As shown, the visualizations using the polyclonal MLC and the pSer19 monoclonal anti-MLC antibodies clearly indicate increases in both total pMLC and Ser19 pMLC with increasing concentrations of NE. The relationship between NE concentration and increases in both Ser19 pMLC and total pMLC (expressed as % change) is shown in FIG. 3A. Similarly, concentration-dependent increases in both Ser19 and total pMLC produced by CAL are shown in FIG. 3B, although compared to the effects of NE (FIG. 4A), CAL appears to produce relatively less of an increase in Ser19 phosphorylation compared to total MLC phosphorylation. In FIG. 3C, the concentration-dependent decreases in both Ser19 and total pMLC produced by SNP (in vessels pre-contracted with 3×10–6 mol/L NE, as in the experiments shown in FIG. 1C).

Example 2

Figure 4:
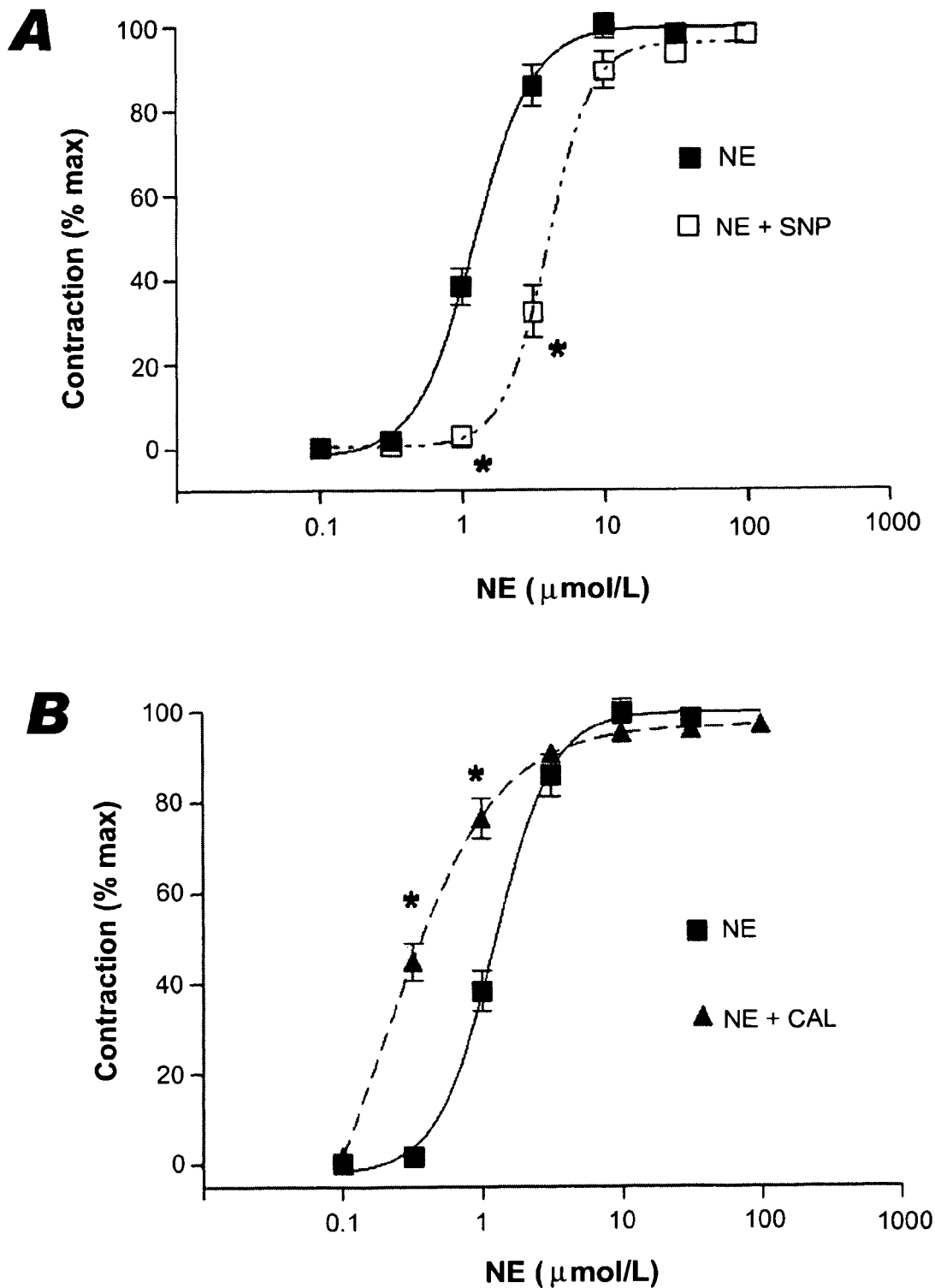
FIG. 4 depicts a series of graphs showing changes in concentration dependent curves. A. Vessels pretreated with $1\times10^{-5}$ mol/L SNP produced a decreased responsiveness to NE as indicated by the rightward shift in the concentration-dependent curve. B. Pretreatment with low-dose ($3\times10^{-8}$ mol/L) CAL produced an increase in the concentration-dependent curve as represented by a leftward shift. C. Low-dose CAL restored NE responsiveness in the condition of NO excess. *P<0.05 compared to NE (■).

Effect of Calyculin A on Norepinephrine Responsiveness under Control and Vasodilatory Shock-Like Conditions As shown in FIG. 4A, the addition of 10$^{-5}$ mol/L SNP resulted in a rightward shift in the NE concentration-response relationship, nearly eliminating the contraction produced by an EC$_{50}$ dose of NE (1×10$^{-6}$ mol/L), and resulting in a significant increase in the EC$_{50}$ for NE to 3.7×10$^{-6}$ mol/L (n=5).

The effects of CAL on NE responsiveness, at the $3\times10^{-8}$ mol/L sub-contracting dose ("low dose" CAL,), is shown in FIG. 4B, and resulted in a leftward shift in the NE concentration-response relationship with an $EC_{50}$ for NE of $1.8\times10^{-7}$ mol/L in the NE+CAL condition (n=5). High dose CAL ($3\times10^{-7}$ mol/L) produced basal contraction and an apparent further leftward shift in NE concentration contraction relationship, resulting in an apparent $EC_{50}$ of $3.4\times10^{-8}$ mol/L (not shown).

Figure 4C:
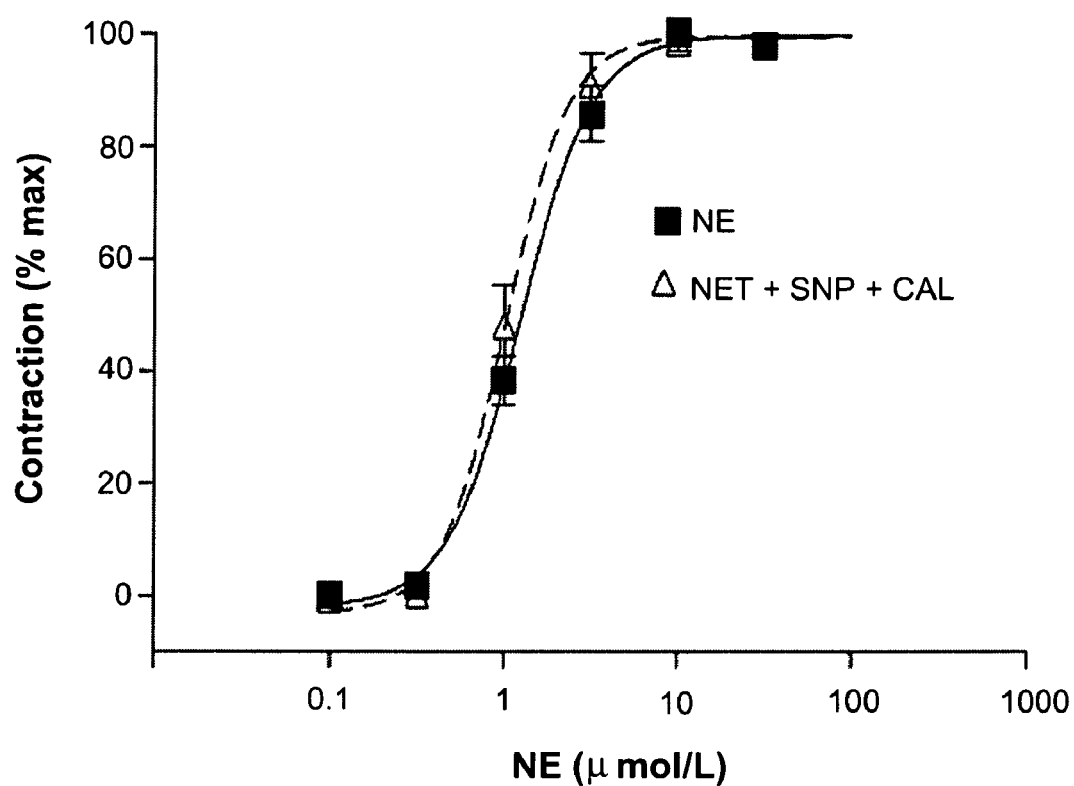

As shown in FIG. 4C, low-dose CAL completely reversed the effect of the NO donor, such that the $EC_{50}$ value for the NE concentration-contraction relationship in the NE+NO+CAL condition was not significantly different when compared to control ($1.0\times10^{-6}$ mol/L, n=5).

Figure 5:
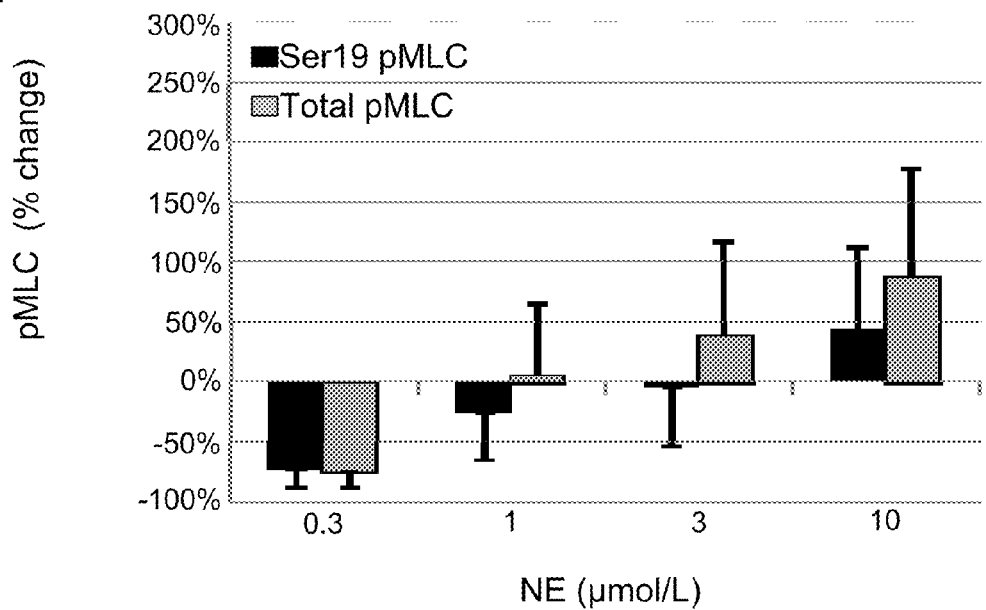
FIG. 5 depicts a series of graphs showing the % change of Ser19 pMLC and total pMLC in response to increasing [NE]. A. A decrease in both Ser19 pMLC and total pMLC (as compared to FIG. 3A) is observed following pretreatment with NO excess ($1\times10^{-5}$ mol/L SNP); B. An increase in both Ser19 pMLC and total pMLC is evidenced in the presence of low dose CAL ($3\times10^{-8}$ mol/L); and C. Both Ser19 pMLC and total pMLC response to increasing [NE] in the presence of both NO excess and low dose CAL
Figure 5:
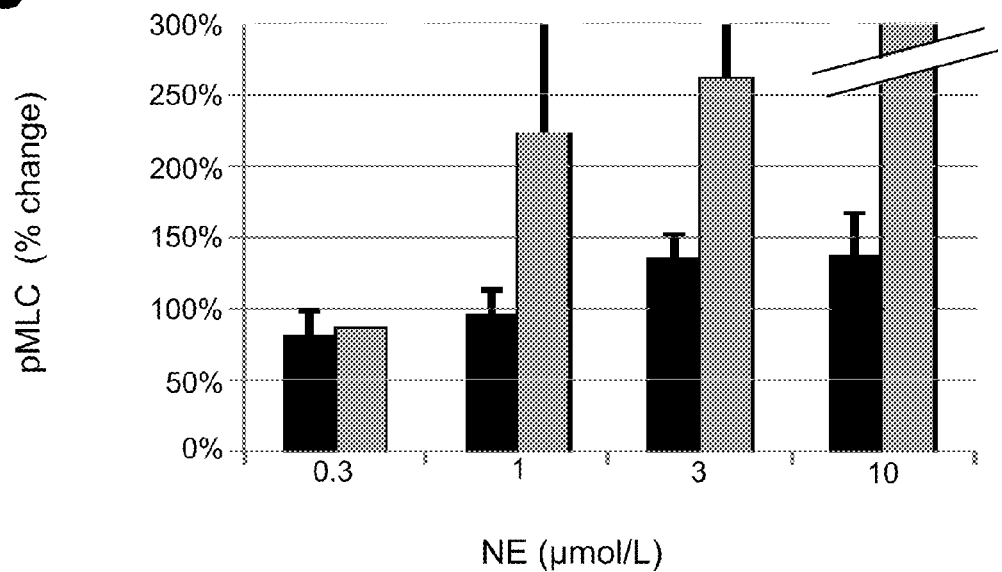
Figure 5C:
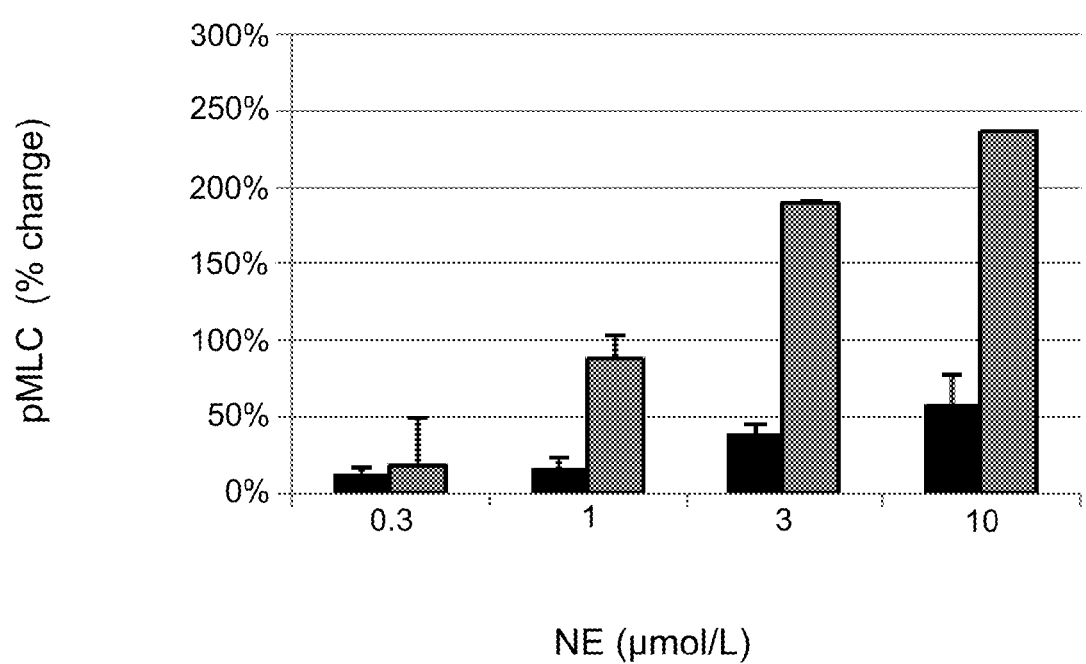

As shown in FIG. 5A, SNP ($10^{-5}$ mol/L) resulted in decreases in NE concentration-dependent Ser19 and total pMLC, in parallel with the decreases in NE concentration dependent contractions shown in FIG. 4A. As shown in FIG. 5B, the increases in NE concentration-dependent contractions produced by low dose CAL shown in FIG. 4B, were similarly accompanied by increases in NE concentration-dependent Ser19 and total pMLC. As shown in FIG. 5C, low dose CAL increased NE concentration-dependent MLC phosphorylation similarly in the presence of SNP (compared to FIG. 5A).

Figure 6:
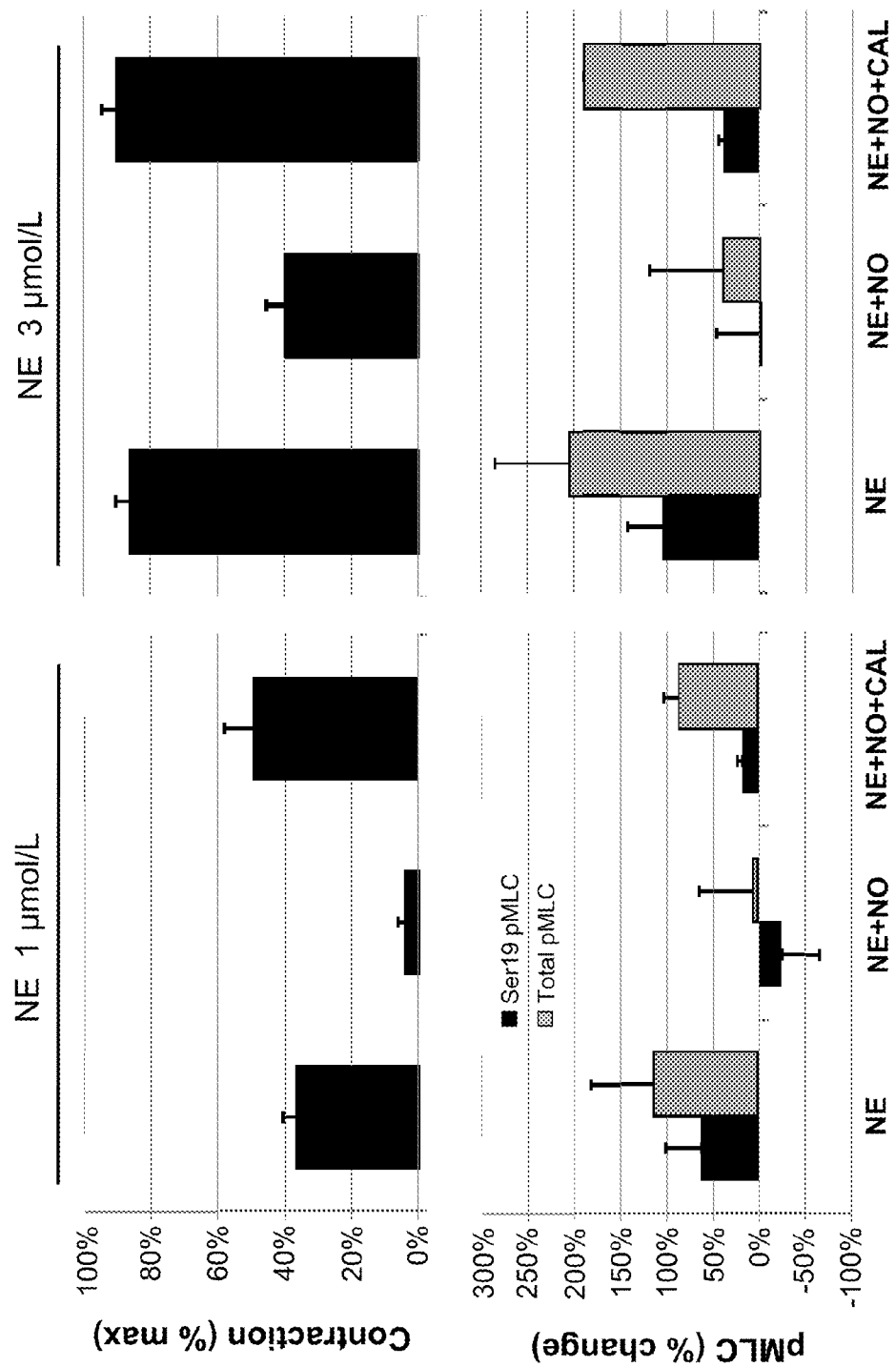
FIG. 6 depicts a series of graphs showing the comparison of the relative changes in contraction (upper panels) and MLC phosphorylation (lower panels) following NE treatment (1 μmol/L, left panels; and 3 μmol/L, right panels) observed in the presence of NO excess, and NO excess including pretreatment with low dose CAL.

As can be seen in FIG. 6, the NE-induced contractions and MLC phosphorylation that are reduced by NO excess ($10^{-5}$ mol/L SNP)—at both the $10^{-6}$ mol/L (approximately $EC_{50}$) and the $3\times10^{-6}$ mol/L (approximately $EC_{90}$) doses of NE—were restored to approximately control levels by low dose CAL.

Discussion for Examples 1-2

Low doses of the myosin light chain phosphatase (MLCP) inhibitor, calyculin A (CAL), which had no constricting effect alone, increased the sensitivity of vascular smooth muscle (VSM) to the alpha adrenergic agonist, norepinephrine, in cannulated mesenteric resistance arteries. Moreover, low dose calyculin completely reversed the decreased responsiveness to norepinephrine in vasodilatory shock-like conditions of excess NO, produced here by the addition of the NO donor sodium nitroprusside. As also shown in these studies, higher doses of CAL alone had a direct constricting effect, evident even in the absence of norepinephrine.

Example 3

In Vivo Studies

The efficacy of non-toxic doses of the MLCP inhibitors in raising blood pressure and increasing catecholamine responsiveness will be determined in normal and septic animals, including animals that have developed clinical septic shock.

Non-fasted male Swiss Webster mice (Charles River Laboratories, Willmington, Mass.) will be used for these studies. Approximately 1 hour prior to study, an intraperitoneal (IP) catheter (3 French catheter; O.D. 0.94 mm×I.D. 0.51 mm; with attachable luer, Instech Solomon, Plymouth Meeting, Pa.) will be surgically implanted under general anesthesia and tunneled through the subcutaneous tissue through a small skin incision so that the distal end exits in the dorsal cervical region. Studies will begin 60 min following catheter insertion, and the implanted catheter will be used to administer the vehicle or study drugs. During the periods of study (up to 2 hours), the animals will be immobilized in a restrainer that allows access to the IP catheter and the tail, which will be used for noninvasive measurement of systemic blood pressure (NIBP device, Model LE5007, Harvard Apparatus, Hollistan, Mass.).

For studies utilizing animals in septic shock, the cecal ligation and puncture (CLP) model described by Chaudry, as modified for mice, will be used. Mice are anesthetized and the cecum is ligated with a 4-0 silk suture and punctured with a #26 needle. The abdominal cavity is then closed in two layers and one ml of saline is administered subcutaneously to replace third space losses. Following CLP, the animals typically stop eating or drinking, and mortality begins within 24 hours and continues for 3 to 5 days. Validation of mouse CLP as a model of septic shock has included 5 of 5 positive blood cultures in CLP mice (with none in sham-treated mice). Organisms isolated from the blood of these animals are common pathogens in human sepsis, including *E. coli, Enterobacter cloacae, Streptococcus faecium*, and *Enterobacter faecium*. CLP is also a relevant model for these studies as evidenced by the development of catecholamine hyporesponsiveness, and hypotension that occurs in the later phases. Varying rates of survival can be achieved in this model by varying the degree of injury and the timing of antibiotic administration.

For all in vivo experiments, animals will be closely observed for sign of increased pain or distress, evidence of excitement or lethargy, agitation or seizures, vomiting or diarrhea, tachypnea, or any other untoward response, including death. Any animal displaying any evidence of pain or suffering will be immediately euthanized by an overdose of IP methohexital (10 mg/kg) and recorded as a mortality.

Initial studies will be directed at determining, in whole animals, the doses of candidate MLCP inhibitors that have immediate or long term toxicity. The effects of subtoxic doses of the inhibitors on blood pressure, catecholamine responsiveness, and tolerance to NO excess will then be studied in healthy animals. Finally, doses of the MLCP inhibitors determined to be safe and effective in healthy animals, will be administered to animals that have developed the clinical picture of septic shock. Such animals may be subjected to cecal ligation and puncture (CLP) in induce the septic shock symptoms.

The whole animal preparation using Swiss Webster mice with an acutely implanted intraperitoneal catheter will be used for these studies. Each experiment will be replicated in 10 mice per group.

In the initial experiments, increasing doses of candidate MLCP inhibitors will be administered IP at 15 min intervals to the point that acute toxicity becomes evident. IP doses at the 15 min intervals will be increased in half log order increments (e.g., 1, 3, 10, 30, etc). The initial dose, determined from isolated vessel studies, will be two log orders lower than the lowest effective dose in vitro. Using Calyculin as an example, the 30 nM dose was effective at increasing catecholamine responsiveness, and reversed NO-induced vasodilation in isolated vessels. Accordingly the initial dose of Calyculin (FW 1009) for the animal studies will be two log orders below 30 nM (≈30 µg/kg) or ≈0.3 µg/kg IP. This will be followed by a 1 µg/kg IP dose at 15 min, 3 µg/kg at 30 min, 10 at 45 min, etc. Control animals will receive identical sequential treatments with IP vehicle. The effects of the increasing doses of the MLCP inhibitors or vehicle on resting blood pressure will be recorded (measured by tail cuff at 5 min intervals). It is expected that animals in the MLCP inhibitor-treated group will demonstrate evidence of hypertension and short term toxicities (or mortality) as the dose of the inhibitor is increased. These experiments will establish the potential therapeutic range of the MLCP inhibitors to be used in subsequent experiments.

Following the initial experiment to establish doses that produce acute toxicity, additional experiments will be conducted to determine if lower doses have any evident long term toxicity. For these experiments animals with acutely implanted IP catheters as described above, will be given a single dose of the MLCP inhibitor in the sub-toxic range, and then observed for two hours for any signs of toxicity. Controls will be treated with vehicle. Blood pressure measurements will be made in both groups. For these experiments the three doses below the established toxic dose will be used. Following this, the animal will be returned to housing and observed daily for one week for any signs of long term toxicity, evidenced by any illness or distress, poor feeding or drinking, etc. Toxicity at each dose will be recorded for each animal, and any dosage which produces evidence of long term toxicity in $\geqq 30\%$ of the animals (i.e., 3 of 10) will be considered toxic and not used in subsequent experiments. Again, any animal showing signs of toxicity, or displaying any evidence of pain or suffering, will be immediately euthanized by an overdose of IP methohexital (10 mg/kg). These studies will establish non toxic doses of the MP inhibitors which can then be tested for efficacy in subsequent experiments.

Non toxic doses of the MP inhibitors (i.e., those which are free of evident short or long term toxicity as above) will be studied for their effects on blood pressure, catecholamine responsiveness, and tolerance to NO excess. Again, animals with acutely implanted catheters will be used for these experiments and treated according to the following protocol: (1) Blood pressure will be recorded at baseline and every 5 min during administration of increasing dose of IP NE. The initial NE dose will be 1 µg/kg (two log orders below the approximate $EC_{50}$ of 1 µM for NE in isolated vessels) with half log order increases in dose every 5 min until resting blood pressure has increased by $\geqq 50\%$. NE concentration pressor response relationships (based on % increase in BP from baseline) will be established for each animal compared before and after MLCP treatment and between groups. (2) Increasing doses of IP sodium nitroprusside (SNP) will then be administered every 5 min beginning with an initial dose of 30 µg/kg (based on the approximate $EC_{50}$ in isolated vessels of 10 µM), again with half log order increases every 5 min until resting blood pressure has decreased by $\geqq 50\%$. NO concentration response relationships based on % decreases in BP from baseline will be established for comparison before and after MLCP treatment and between treated and control group. (3) Following this initial assessment of NE and NO concentration response relationships, animals will be treated with either a single non toxic dose of the MP inhibitor IP or vehicle (controls) followed at 30 min by reassessment of NE and NO responsiveness as in (1) and (2). This maximum dose of the MP inhibitor that did not produce evidence of toxicity will be studied first. If this dose produces measurable effects on baseline blood pressure, or NE and/or NO concentration response relationships, lower doses of the inhibitor will be studied in subsequent experiments to establish the lowest effective dose.

For all in vivo experiments, animals will be closely observed for sign of pain or distress, evidence of excitement or lethargy, agitation or seizures, vomiting or diarrhea, tachypnea, or any other untoward response, including death. Any animal displaying any evidence of pain or suffering will be immediately euthanized by an overdosage with IP methohexital (10 mg/kg) and recorded as a mortality.

The cecal ligation and puncture (CLP) model of septic shock described above will be used to test the safety and efficacy of the MLCP inhibitors on blood pressure, catecholamine responsiveness, and tolerance to NO excess. The effects of doses of MLCP inhibitors determined to be safe and effective in healthy animals will be tested for safety and efficacy in septic animals following CLP. A survival CLP model will be used, in which antibiotics are delayed, but sufficient to result in long term survival (1 week) of approximately 50% (30 to 70%) of the animals. Controls will include both sham operated and vehicle treated animals. Testing the MLCP inhibitors in this model should provide the sensitivity needed to detect any significant sub clinical toxicity that may negatively influence long term survival. A vasoconstricting effect of an MLCP inhibitor that results in maldistribution of blood flow, for example, which may not have been evident in the healthy or sham operated animal groups, should produce a measureable effect on long term survival in a 50% survival model, or would be unlikely to be of clinical consequence. Similarly, subclinical hepatotoxicity may not become evident until animals become septic, but this again should influence long term survival if it is important. Experiments will otherwise be conducted using the same protocol as that used in the healthy subject described above, again with inclusion of a two by two design involving sham and CLP operated, and MLCP- and vehicle-treated groups. Baseline blood pressure, catecholamine responsiveness (based on % change), and tolerance to NO donors will be studied. It is expected that baseline blood pressure may be different between the CLP and sham operated groups, particularly if some animals in the CLP group have developed septic shock. And it is understood that this difference could potentially confound the interpretation of % changes in blood pressure from baseline as an index of catecholamine and NO sensitivity between CLP and sham operated animals. However, baseline blood pressure should be similar in the CLP groups and differences in blood pressure responses between vehicle and MLCP inhibitor-treated animals should be readily interpretable. The efficacy of the MLCP inhibitors in septic animals, a primary purpose of the experiment, should thus still be easily assessed.

Doses of MLCP inhibitors determined to be safe and effective in septic animals following CLP using the 50% survival CLP model above will be further tested for both safety and efficacy in animals in which antibiotics have been withheld and hypotension has developed. To this end, blood pressure will be measured in a group of animals prior to CLP and then daily after CLP until baseline blood pressure has declined by 25-50%. Animals will then be implanted with the intraperitoneal catheter and the effects of subtoxic and effective doses of the MLCP inhibitors will be tested for effects on blood pressure and catecholamine sensitivity. Tolerance to NO excess will not be tested in this already hypotensive model, and non-hypotensive sham operated animals will not be used as a comparator group. It is anticipated that MLCP inhibitor-treated groups of animals with septic shock will manifest increases in blood pressure and catecholamine sensitivity compared to the vehicle-treated controls. Time until death in the MLCP inhibitor- and vehicle-treated groups will also be followed to assess for any previously undetected toxicity.

Subsequent to these studies, and with appropriate approval, human studies will be conducted to determine the safety and efficacy of the MLCP inhibitor in humans.

REFERENCES

1. Landry D W, Oliver J A (2001) The pathogenesis of vasodilatory shock. *N Engl J Med.* 345: 588-595.

2. Boyle, W A, Parvathaneni L S, Bourlier V, Sauter C, Laubach V E, and Cobb J P (2000) iNOS gene expression modulates microvascular responsiveness in endotoxin-challenged mice. *Circ Res.* 87:18-24.
3. The American Heart Association in Collaboration with the International Liaison Committee on Resuscitation (IL-COR). Part 6: Advanced cardiovascular life support. Section 6: Pharmacology II: Agents to optimize cardiac output and blood pressure (2000) *Resuscitation.* 46: 55-62.
4. Chernow B, Rothl B L (1986) Pharmacological manipulation of the peripheral vasculature in shock: clinical and experimental approaches. *Circ Shock.* 18: 141-155.
5. Dunser M W, Mayr A J, Ulmer H, Knotzer H, Sumann G, Pajk W, Friesenecker B, Hasibeder, W R (2003) Arginine vasopressin in advanced vasodilatory shock *Circulation.* 107(18): 2313-2319.
6. Benedict C R, Rose J A (1992) Arterial norepinephrine changes in patients with septic shock. *Circ Shock.* 38: 165-172.
7. Surks H K, Mochizuki N, Kasai Y (1999) Regulation of Myosin phosphatase by a specific interaction with cGMP-dependent protein kinase Iα. *Science.* 286: 1583-1587.
8. Hollenberg S M, Cunnion R E, Zimmerberg J (1993) Nitric oxide synthase inhibition reverses arteriolar hyporesponsiveness to catecholamines in septic rats. *Am J Physiol.* 264: H660-H663.
9. Kilbourn R (1999) Nitric oxide synthase inhibitors—a mechanism-based treatment of septic shock. *Crit Care Med.* 27: 857-858.
10. Cobb J P (1999) Use of nitric oxide synthase inhibitors to treat septic shock: the light has changed from yellow to red. *Crit Care Med.* 27: 855-856.
11. Kato Y, Fusetani N, Matsunaga S, Hashimoto K (1988) Calyculins, potent antitumor metabolites from the marine sponge Discodermia calyx: Biological activities. *Drugs Expl Clin Res.* 65: 723-728.
12. Ishihara H, Ozaki H, Sato K, Hori M, Karaki H, Watabe S, Kato Y, Fusetani N, Hashimoto K, Uemura D, Hartshorne D J (1989) Calcium-independent activation of contractile apparatus in smooth muscle by Calyculin-A. *J Pharmacol Exp Ther.* 250: 388-396.
13. Karim S M, Rhee A Y, Given A M, Faulx M D, Hoit B D, Brozovich F V (2004) Vascular reactivity in heart failure: role of MLCP. *Circ Res.* 95: 612-618.
14. Alioua A, Tanaka Y, Wallner M, Hofmann F, Ruth P, Meera P, Toro L (1998) The large conductance, voltage-dependent, and calcium-sensitive K+ channel is a target of cGMP-dependent protein kinase phosphorylation in vivo. *J Biol Chem.* 273: 32950-3295.
15. Schmidt H H, Lohmann S M, Walter U (1993) The NO and cGMP signal translocation system: Regulation and mechanism of action. *Biochim Biophys Acta.* 1178: 153-175.
16. Fukao M, Mason H S, Britton F C, Kenyon J L, Horowitz B, Keef K D (1999) Cyclic GMP-dependent protein kinase activates BKCa channels expressed in mammalian cells by direct phosphorylation at serine 1072. *J Biol Chem.* 274: 10927-10935.
17. Lincoln T M, Dey N, Sellak H (2001) cGMP-dependent protein kinase signaling mechanism in smooth muscle: from the regulation of tone to gene expression. *J Appl Physiol.* 91: 421-1430.
18. Yano Y, Sakon M, Kambayashi J, Kawasaki T, Senda T, Tanaka K, Yamada F, Shibata N (1995) Cytoskeletal reorganization of human platelets induced by the protein phosphatase 1/2A inhibitors okadaic acid and calyculin A. *Biochem J.* 307: 439-449.
19. Zhao K, Huang X, Liu J, Huang Q, Jin C, Jiang Y, Jin J, Zhao G (2002) New approach to treatment of shock-restitution of vasoreactivity. *Shock.* 18: 189-192.
20. Webb R C (2003) Smooth muscle contraction and relaxation. *Adv Phys Ed.* 27: 201-206.
21. Somlyo A P, Somlyo A V (2003) Ca sensitivity of smooth muscle and nonmuscle myosin II. *Physiol Rev.* 83: 1325-1358.
22. Leone M, Boyle W A (2006) Decreased vasopressin responsiveness in vasodilatory septic shock-like conditions. *Crit Care Med.* 34: 1126-1230.
23. Murphy M E, Brayden J E (1995) Nitric oxide hyperpolarizes rabbit mesenteric arteries via ATP-sensitive potassium channels. *J Physiol.* 486: 47-58.
24. Quayle J M, Nelson M T, Standen N B (1997) ATP-sensitive and inwardly rectifying potassium channels in smooth muscle. *Physiol Rev.* 77: 1165-1232.
25. Etter E F, Eto M, Wardle R L, Brautigan D L, Murphy R A (2001) Activation of myosin light chain phosphatase in intact arterial smooth muscle during nitric oxide-induced relaxation. *J Biol Chem.* 276: 34681-34685.
26. Jaggar J H, Porter V A, Lederer W J, Nelson M T (2000) Calcium sparks in smooth muscle. *Am J Physiol.* 278: C235-C256.
27. Parekh A B, Terlau H, Stuhmer W (1993) Depletion of InsP3 stores activates a Ca and K current by means of a phosphatase and a diffusible messenger. *Nature.* 364: 814-818.
28. Evans N E, Forth M K L, Simpson A K, Mason M J (2005) Inhibition by calyculin A and okadaic acid of the Ca release-activated Ca entry pathway in rat basophilic leukemia cells: Evidence for regulation by type 1/2A serine/threonine phosphatase activity. *Biochim Biophys Acta.* 1718: 32-43.
29. Bolz S S, Vogel L, Sollinger D, Derwand R, deWit C, Loirand G, Pohl U (2003) Nitric oxide-induced decreased in calcium sensitivity of resistance arteries is attributable to activation of the myosin light chain phosphatase and antagonized by the RhoA/Rho Kinase pathway. *Circulation.* 107: 3081-3087.
30. Dimopoulos G J, Semba S, Kitazawa K, Eto M, Kitazawa T (2007) Ca-dependent rapid Ca sensitization of contraction in arterial smooth muscle. *Circ Res.* 100: 121-129.

What is claimed is:

1. A method of decreasing the lumenal diameter of a blood vessel that has lost sensitivity to a vasoconstrictor, the method comprising contacting the vessel with a sub-constricting amount of calyculin A and a vasoconstrictor, wherein the sub-constricting amount is sufficient to substantially restore blood vessel sensitivity to the vasoconstrictor, but does not cause contraction of the blood vessel.

2. A method of substantially restoring blood vessel sensitivity to a vasoconstrictor, the method comprising contacting the vessel that has lost sensitivity to the vasoconstrictor with a sub-constricting amount of calyculin A and the vasoconstrictor, such that the sensitivity of the blood vessel to the vasoconstrictor is substantially restored.

3. A method of treating vasodilatory shock in a subject, the method comprising administering a sub-constricting amount of calyculin A to the subject and administering a vasoconstrictor that a blood vessel in the subject has lost sensitivity to, thereby restoring the sensitivity of the blood vessel to the vasoconstrictor.

* * * * *